(12) United States Patent
Klug et al.

(10) Patent No.: US 9,090,467 B2
(45) Date of Patent: Jul. 28, 2015

(54) METHOD OF STABILIZING HYDROGEN PEROXIDE OR HYDROGEN PEROXIDE DONOR SUBSTANCES WITH HYDROXYPYRIDONES OR SALTS THEROF

(75) Inventors: Peter Klug, Grossostheim (DE); Maurice Frederic Pilz, Frankfurt am Main (DE); Ute Back, Blankenbach (DE)

(73) Assignee: Clariant Finance (BVI) Limited, Tortola (VG)

( * ) Notice: Subject to any disclaimer, the term of this patent is extended or adjusted under 35 U.S.C. 154(b) by 161 days.

(21) Appl. No.: 13/812,114

(22) PCT Filed: Jul. 15, 2011

(86) PCT No.: PCT/EP2011/003537
§ 371 (c)(1),
(2), (4) Date: Mar. 20, 2013

(87) PCT Pub. No.: WO2012/019689
PCT Pub. Date: Feb. 16, 2012

(65) Prior Publication Data
US 2013/0236383 A1   Sep. 12, 2013

(30) Foreign Application Priority Data

Jul. 27, 2010 (DE) .......................... 10 2010 032 371
Dec. 17, 2010 (DE) .......................... 10 2010 054 865

(51) Int. Cl.
| | | |
|---|---|---|
| C01B 15/037 | (2006.01) | |
| A61K 8/22 | (2006.01) | |
| A61K 8/49 | (2006.01) | |
| A61Q 5/08 | (2006.01) | |
| A61Q 5/10 | (2006.01) | |
| C01B 15/08 | (2006.01) | |
| C01B 15/12 | (2006.01) | |
| A61Q 11/00 | (2006.01) | |

(52) U.S. Cl.
CPC ................ C01B 15/037 (2013.01); A61K 8/22 (2013.01); A61K 8/4926 (2013.01); A61Q 5/08 (2013.01); A61Q 5/10 (2013.01); C01B 15/085 (2013.01); C01B 15/123 (2013.01); A61K 2800/52 (2013.01); A61Q 11/00 (2013.01)

(58) Field of Classification Search
CPC ....................................................... C01B 15/37
See application file for complete search history.

(56) References Cited

U.S. PATENT DOCUMENTS

| | | | |
|---|---|---|---|
| 4,804,705 | A | 2/1989 | Pum et al. |
| 5,206,385 | A | 4/1993 | Login et al. |
| 6,083,422 | A | 7/2000 | Ambuter et al. |
| 6,180,118 | B1 | 1/2001 | Maubru |
| 2004/0074015 | A1 | 4/2004 | Kravtchenko et al. |
| 2006/0009371 | A1 | 1/2006 | Wang et al. |
| 2011/0003010 | A1 | 1/2011 | Klug et al. |
| 2013/0272984 | A1 | 10/2013 | Klug et al. |
| 2014/0147402 | A1 | 5/2014 | Klug et al. |

FOREIGN PATENT DOCUMENTS

| | | |
|---|---|---|
| DE | 102010054918 | 6/2011 |
| EP | 0 829 258 | 3/1998 |
| EP | 1 347 736 | 7/2002 |
| FR | 2 804 863 | 8/2001 |
| WO | WO 02/051369 | 7/2002 |
| WO | WO 02/051961 | 7/2002 |
| WO | WO 2009/015856 | 2/2009 |

OTHER PUBLICATIONS

English Abstract for DE102010054918, dated Jun. 30, 2011.
English Abstract for FR 2 804 863, dated Aug. 17, 2001.
Karlheinz Schrader, Andreas Domsch, Cosmetology—Theory and Practice, vol. II, Verlag für chemische Industrie, Augsburg, 2005, pp. 114-115.
Karlheinz Schrader, Andreas Domsch, Cosmetology—Theory and Practice, vol. II, Verlag für chemische Industrie, Augsburg, 2005, p. 145.
International Search Report for PCT/EP2011/003537, dated Mar. 6, 2012.
International Preliminary Report on Patentability for PCT/EP2011/003537, dated Jan. 29, 2013.
International Search Report for PCT/EP2011/003536, dated Mar. 5, 2012.
International Preliminary Report on Patentability for PCT/EP2011/003536, dated Feb. 14, 2013.
International Search Report for PCT/EP2011/006277, dated Mar. 5, 2012.
International Preliminary Report on Patentability for PCT/EP2011/006277, dated Jun. 20, 2013.

*Primary Examiner* — Melissa Swain
(74) *Attorney, Agent, or Firm* — Tod A. Waldrop

(57) ABSTRACT

A description is given of the use of hydroxypyridones or the salts thereof for stabilizing hydrogen peroxide or hydrogen peroxide donor substances. The stabilization takes place preferably in aqueous compositions.

11 Claims, No Drawings

METHOD OF STABILIZING HYDROGEN PEROXIDE OR HYDROGEN PEROXIDE DONOR SUBSTANCES WITH HYDROXYPYRIDONES OR SALTS THEROF

The present invention relates to the use of hydroxypyridones or salts thereof for stabilizing hydrogen peroxide or hydrogen peroxide donor substances.

Compositions and in particular aqueous compositions comprising hydrogen peroxide are used in a variety of applications. They are used in cosmetic compositions e.g. as bleaching composition for hair, as developer component in hair colorants, but also as a component for hair fixing in permanent wave formulations. Further applications are e.g. dental bleach compositions. Hydrogen peroxide-containing compositions are also represented in industrial cleaning and in domestic cleaning and in the bleaching of textiles.

However, the stability of the hydrogen peroxide or of the hydrogen peroxide donor substances in the compositions is often unsatisfactory.

It was therefore the object to provide new stabilizers for hydrogen peroxide and hydrogen peroxide donor substances.

Surprisingly, it has now been found that this object is achieved through the use of hydroxypyridones or salts thereof.

The invention therefore provides the use of one or more substances selected from the group consisting of hydroxypyridones and salts thereof (component d)) for stabilizing one or more substances selected from the group consisting of hydrogen peroxide and hydrogen peroxide donor substances (component a)).

Hereinbelow, the one or more substances selected from the group consisting of hydroxypyridones and salts thereof are also referred to as substances of component d).

The one or more substances selected from the group consisting of hydrogen peroxide and hydrogen peroxide donor substances are also referred to hereinbelow as substances of component a).

By virtue of the use according to the invention, the hydrogen peroxide and/or the hydrogen peroxide donor substances are stabilized, as a result of which, for example, the storage stability of corresponding compositions is increased. The increased stability of the hydrogen peroxide and/or of the hydrogen peroxide donor substances in these compositions can result either in the effect of the ingredients being enhanced, such as e.g. their cleaning or bleaching performance, or the useful life of such formulations being increased.

EP 1 347 736 describes oxidative compositions for hair treatment which comprise stabilizers for hydrogen peroxide based on pyrophosphate, stannates, phenacetin or oxyquinoline or combinations thereof.

Preferably, the one or more substances of component a) is or are selected from the group consisting of hydrogen peroxide, urea peroxide, perborates, persulfates and mixtures thereof. The substance of component a) is particularly preferably hydrogen peroxide.

Preferably, the one or more substances of component d) is or are selected from compounds of the formula (I) and salts thereof

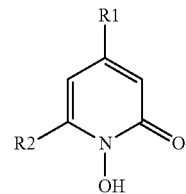

in which R1 is H or a $C_1$-$C_4$-alkyl radical and R2 is H, an unsubstituted or halogen-substituted, branched or unbranched $C_1$-$C_{20}$-alkyl radical, an unsubstituted or halogen-substituted $C_5$-$C_8$-cycloalkyl radical, an unsubstituted or halogen-substituted $C_6$-$C_{10}$-aryl radical or an unsubstituted or halogen-substituted, branched or unbranched $C_7$-$C_{20}$-aralkyl radical.

Preferably, the radicals R2 are not halogen-substituted.

In a preferred embodiment of the invention, the one or more compounds of component d) is or are present in the form of the acid (compounds of the formula (I)) or in the form of their alkali metal, alkaline earth metal or amine salts or their salts with polymeric counterions.

In the one or more compounds of the formula (I) or in their salts, R1 is preferably methyl and R2 is preferably cyclohexyl or 2,4,4-trimethylpentyl.

The compounds of the formula (I) are particularly preferably present in the form of their alkanolamine salts and especially preferably present in the form of their monoethanolamine salts. Examples of salts of this type are mentioned in DE 2234009.

Particular preference is given here to 4-methyl-6-(2,4,4-trimethylpentyl)-1-hydroxy-2-pyridone, the monoethanolamine salt of 4-methyl-6-(2,4,4-trimethylpentyl)-1-hydroxy-2-pyridone (Octopirox®, Clariant), and 4-methyl-6-(cyclohexyl)-1-hydroxy-2-pyridone and the monoethanolamine salt of 4-methyl-6-(cyclohexyl)-1-hydroxy-2-pyridone (Ciclopirox®, Sanofi-Aventis).

These substances can be obtained in accordance with processes known from the literature, cf. in this regard the references given in DE 2234009.

The use according to the invention preferably takes place in aqueous compositions.

Preferably, the water is present in an amount of 40% by weight or more and particularly preferably in an amount of 50% by weight or more in the aqueous compositions, based on the total weight of the aqueous compositions.

The one or more substances selected from the group consisting of hydrogen peroxide and hydrogen peroxide donor substances of component a) are present preferably in amounts of from 0.5 to 20% by weight, particularly preferably in amounts of from 1 to 10% by weight, especially preferably in amounts of from 1.5 to 7% by weight and extraordinarily preferably in amounts of from 2 to 7% by weight, in the aqueous compositions, based on the total weight of the aqueous compositions.

Among these, the substance of component a) is in turn preferably hydrogen peroxide, which is present preferably in amounts of from 0.5 to 20% by weight, particularly preferably in amounts of from 1 to 10% by weight, especially preferably in amounts of from 1.5 to 7% by weight and extraordinarily preferably in amounts of from 2 to 7% by weight, in the aqueous compositions, based on the total weight of the aqueous compositions.

In the aqueous compositions, the one or more substances of component d) is or are present in amounts of preferably from 0.1 to 20 000 ppm (0.00001 to 2% by weight), particularly preferably in amounts of from 0.5 to 1000 ppm (0.00005 to 0.1% by weight) and particularly preferably in amounts of from 0.5 to 100 ppm (0.00005 to 0.01% by weight), based on the total weight of the aqueous compositions.

The hydroxypyridones or their salts can be combined with further stabilizers for the use according to the invention. Further suitable stabilizers are e.g. polyphosphates or their alkali metal or alkaline earth metal salts, alkali metal or alkaline earth metal stannates, phenacetin and its acid salts, and oxyquinoline and its acid salts.

The aqueous compositions can comprise, as further auxiliaries and additives, oil bodies, silicone oils, waxes, surfactants, emulsifiers, coemulsifiers, solubilizers, cationic polymers, film formers, superfatting agents, refatting agents, antimicrobial active ingredients, humectants, solvents, dyes, fragrances, pearlizing agents and/or opacifiers.

The aqueous compositions can comprise organic solvents. In principle, suitable organic solvents are all mono- or polyhydric alcohols. Preference is given to using alcohols having 1 to 4 carbon atoms such as ethanol, propanol, isopropanol, n-butanol, isobutanol, t-butanol, glycerol, 1,2- and 1,3-propanediol and mixtures of said alcohols. Further preferred alcohols are polyethylene glycols with a relative molecular mass below 2000. In particular, a use of polyethylene glycol with a relative molecular mass between 200 and 600 and in amounts up to 45.0% by weight and of polyethylene glycol with a relative molecular mass between 400 and 600 in amounts of from 5.0 to 25.0% by weight is preferred. Further suitable solvents are, for example, triacetin (glycerol triacetate) and 1-methoxy-2-propanol.

The aqueous compositions may e.g. also be aqueous-surface-active or aqueous-alcoholic compositions, or emulsions.

The acids or alkalis used for adjusting the pH of the aqueous compositions are preferably mineral acids, in particular HCl, inorganic bases, in particular NaOH or KOH, and organic acids, in particular citric acid.

The aqueous compositions preferably have a pH of from 2 to 11, particularly preferably from 7 to 11, especially preferably from 8 to 11 and extraordinarily preferably from 8.5 to 11.

The stabilization according to the invention of the hydrogen peroxide or of the hydrogen peroxide donor substances can be utilized e.g. in the following applications: in bleaching compositions for the hair or the teeth, in oxidative hair colors, for the use of the hydrogen peroxide or of the hydrogen peroxide donor substances as fixing component for permanent wave formulations, in domestic cleaners, in oxidative cleaning formulations, in compositions for the oxidative bleaching of fibers or textiles, in prewash sprays, stain removers, surface cleaners or toilet cleaners.

The examples and applications below are intended to explain the invention in more detail without, however, limiting it thereto. All of the percentages are percent by weight (% by wt.), unless explicitly stated otherwise.

EXPERIMENTAL EXAMPLES

Example 1

Hydrogen peroxide solution from Solvay (35% by weight in water) or from Merck (35% by weight in water) was diluted to a hydrogen peroxide content of about 6.0% by weight with demineralized water and adjusted to a pH of 9.0 using sodium hydroxide solution (20% by weight). Further solutions were in each case additivized with 8 ppm of 4-methyl-6-(2,4,4-trimethylpentyl)-1-hydroxy-2-pyridone (additive A, dissolved in propylene glycol). The solutions were stored at room temperature (20° C.) and 40° C. for one week and the hydrogen peroxide content was measured before and after storage (see table 1).

TABLE 1

Results of the measurement of the hydrogen peroxide content

| Hydrogen peroxide | Additive A | Hydrogen peroxide content immediately [% by weight] | Hydrogen peroxide content after 1 week 20° C. [% by wt.] | Hydrogen peroxide content after 1 week 40° C. [% by wt.] |
| --- | --- | --- | --- | --- |
| Solvay (35% by wt.) | No | 6.3 | 4.8 | <0.1 |
| Solvay (35% by wt.) | Yes | 6.0 | 6.1 | 5.9 |
| Merck (35% by wt.) | No | 5.9 | 3.9 | 2.0 |
| Merck (35% by wt.) | Yes | 6.1 | 6.1 | 5.8 |

Example 2

Hydrogen peroxide solution from Solvay (35% by weight in water) or from Merck (35% by weight in water), a solution of sodium $C_{14-17}$-alkyl sec-sulfonate (Hostapur® SAS 30) and demineralized water were mixed such that a hydrogen peroxide content of about 6.0% by weight and a content of sodium $C_{14-17}$ alkyl sec-sulfonate of 5.0% by weight resulted. The mixture was then adjusted to a pH of 9.0 with sodium hydroxide solution (20% by weight). Further solutions were in each case additivized with 7 ppm of 4-methyl-6-(2,4,4-trimethylpentyl)-1-hydroxy-2-pyridone (additive A, dissolved in propylene glycol). The solutions were stored at room temperature and 40° C. for 1 week and the hydrogen peroxide content was measured before and after storage (see table 2).

TABLE 2

Results of the measurement of the hydrogen peroxide content

| Hydrogen peroxide | Additive A | Hydrogen peroxide content immediately [% by weight] | Hydrogen peroxide content after 1 week 20° C. [% by wt.] | Hydrogen peroxide content after 1 week 40° C. [% by wt.] |
| --- | --- | --- | --- | --- |
| Solvay (35% by wt.) | No | 6.1 | 3.7 | 0.1 |
| Solvay (35% by wt.) | Yes | 6.0 | 6.1 | 5.8 |
| Merck (35% by wt.) | No | 5.9 | 4.2 | 1.4 |
| Merck (35% by wt.) | Yes | 6.0 | 6.1 | 5.2 |

The results of examples 1 and 2 show that 4-methyl-6-(2,4,4-trimethylpentyl)-1-hydroxy-2-pyridone can significantly increase the storage stability of hydrogen peroxide solutions at a high pH both at room temperature and at 40° C.

Example 3

Hydrogen Peroxide Gel Thickened with a Sulfonate Polymer

Formulation:

| | |
|---|---|
| Water, demineralized | ad 100% by wt. |
| Hydrogen peroxide solution (Solvay, 35% strength by weight, aqueous) | 17% by wt. |
| Aristoflex ® AVS | 1.0% by wt. |
| Sodium acryloyldimethyltaurate/VP crosspolymer | |
| 4-methyl-6-(2,4,4-trimethylpentyl)-1-hydroxy-2-pyridone | 0.00081% by wt. |

The formulation was prepared by dissolving the polymeric thickener in water and subsequent mixing in of the hydrogen peroxide solution. The start pH in each case was then adjusted using 10% strength by weight aqueous sodium hydroxide solution. The formulation was prepared in each case with and without the addition of 8.1 ppm (0.00081% by weight) of 4-methyl-6-(2,4,4-trimethylpentyl)-1-hydroxy-2-pyridone.

For this purpose, 10 ml of a 0.1% strength by weight solution of the stabilizer in propylene glycol were dissolved in 1 liter of water and this solution was used as water phase. A blank experiment with propylene glycol ruled out an influence from the solvent. At the same time, the hydrogen peroxide content was in each case determined iodometrically (see table 3).

TABLE 3

Results of the measurement of the hydrogen peroxide content

| Start pH | 8.1 ppm (=0.00081% by wt.) of 4-methyl-6-(2,4,4-trimethylpentyl)-1-hydroxy-2-pyridone | Hydrogen peroxide content immediately [% by wt.] | Hydrogen peroxide content after 2 weeks at 25° C. [% by wt.] |
|---|---|---|---|
| 9.0 | no | 6.0 | 0.4 |
| 9.0 | yes | 6.0 | 6.0 |

It is clear from table 3 that the hydrogen peroxide content of the solution without stabilizer drops from the starting value 6.0% by weight to 0.4% by weight, whereas with stabilizer the initial value of 6.0% by weight is maintained.

Similar results to those described in examples 1-3 were also obtained when using 10 ppm of 4-methyl-6-(2,4,4-trimethylpentyl)-1-hydroxy-2-pyridone, monoethanolamine salt (Octopirox®).

The invention claimed is:

1. A method for stabilizing at least one substance selected from the group consisting of hydrogen peroxide and hydrogen peroxide donor substances (component a)) comprising the step of adding at least one substance selected from the group consisting of hydroxypyridones and salts thereof (component d)) to an aqueous composition.

2. The method as claimed in claim 1, wherein the at least one substance of component a) is selected from the group consisting of hydrogen peroxide, urea peroxide, perborates, persulfates and mixtures thereof.

3. The method as claimed in claim 1, wherein the at least one substance of component a) is hydrogen peroxide.

4. The method as claimed in claim 1, wherein the at least one substance of component d) is selected from compounds of the formula (I) and salts thereof

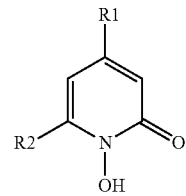

(I)

in which R1 is H or a $C_1$-$C_4$-alkyl radical and R2 is H, an unsubstituted or halogen-substituted, branched or unbranched $C_1$-$C_{20}$-alkyl radical, an unsubstituted or halogen-substituted $C_5$-$C_8$-cycloalkyl radical, an unsubstituted or halogen-substituted $C_6$-$C_{10}$-aryl radical or an unsubstituted or halogen-substituted, branched or unbranched $C_7$-$C_{20}$-aralkyl radical.

5. The method as claimed in claim 1, wherein the at least one compound of component d) is present in the form of the acid or in the form of the alkali metal, alkaline earth metal or amine salts or in the form of the salts with polymeric counterions.

6. The method as claimed in claim 4, wherein, in the at least one compound of the formula (I) or in the salts, R1 is methyl and R2 is cyclohexyl or 2,4,4-trim ethyl pentyl.

7. The method as claimed in claim 1, wherein the substance of component a) is hydrogen peroxide and the hydrogen peroxide is present in an amount of from 0.5 to 20% by weight in the aqueous composition, based on the total weight of the aqueous composition.

8. The method as claimed in claim 1, wherein the at least one substance of component d) is present in an amount of from 0.1 ppm to 2% by weight in the aqueous composition, based on the total weight of the aqueous composition.

9. The method as claimed in claim 8, wherein the at least one substance of component d) is present in an amount of from 0.5 to 100 ppm in the aqueous composition, based on the total weight of the aqueous composition.

10. The method as claimed in claim 1, wherein the aqueous composition has a pH of from 2 to 11.

11. The method as claimed in claim 10, wherein the aqueous composition has a pH of from 7 to 11.

* * * * *